United States Patent [19]

Prentice et al.

[11] 4,328,317

[45] May 4, 1982

[54] CONTINUOUS CHEMICAL CONVERSION OR FERMENTATION APPARATUS

[75] Inventors: Robert C. Prentice, Terril; Dale W. Mastarone, Spencer, both of Iowa

[73] Assignee: Solargizer International, Inc., Bloomington, Minn.

[21] Appl. No.: 136,053

[22] Filed: Mar. 31, 1980

[51] Int. Cl.³ .............................................. C12M 1/14
[52] U.S. Cl. .................................... 435/310; 435/307; 435/309; 435/315; 435/316
[58] Field of Search ............... 435/304, 305, 307, 308, 435/309, 310, 313, 315, 316, 813

[56] References Cited

U.S. PATENT DOCUMENTS

| | | | |
|---|---|---|---|
| 350,472 | 10/1886 | Baldwin | 435/304 |
| 409,956 | 8/1889 | Gent | 435/304 |
| 749,087 | 1/1904 | Neubert et al. | 435/307 |
| 2,146,326 | 2/1939 | Berguis et al. | |
| 2,155,134 | 4/1936 | Karsch | |
| 2,440,925 | 5/1948 | Boeckeler | |
| 2,450,218 | 9/1948 | Victorero | |
| 2,451,156 | 10/1948 | De Mattos | |
| 3,028,314 | 4/1962 | Means et al. | |
| 3,032,476 | 5/1962 | Sher | |
| 3,033,762 | 5/1962 | Schwaiger et al. | 435/308 |
| 3,062,724 | 11/1962 | Rensser | |
| 3,413,124 | 11/1968 | Akin | |
| 3,575,813 | 4/1971 | Rothmayr | 435/313 X |
| 3,699,840 | 6/1972 | Hatcher | |
| 3,705,841 | 12/1972 | Lumb et al. | |
| 3,716,375 | 2/1973 | Hancock | |
| 3,743,582 | 7/1973 | Kitai et al. | |
| 3,801,468 | 4/1974 | Lumb et al. | |
| 3,985,622 | 10/1976 | Hawkins | |

Primary Examiner—Robert J. Warden
Attorney, Agent, or Firm—Merchant, Gould, Smith, Edell, Welter & Schmidt

[57] ABSTRACT

The disclosed continuously operated apparatus (10) is suitable for a variety of chemical processes, including enzymatic conversion of substrates to, for example, organic liquids such as alkanols. In this apparatus (10):

A generally vertically disposed fermentation tower (11) defines a generally vertically extending space containing a plurality of vertically arranged, tray-like zones (15a–15h) for the temporary retention, continuous receiving, and continuous gravity discharge of a feedstock. A typical zone, e.g. zone (15c) has a generally horizontal floor (65c) having a drain opening (165c) for the continuous discharge by gravity of partially converted feedstock to the next lower zone (15d). Each zone (e.g. 15c) is further divided into continuously movable segments by movable partitions (157c) for advancing the fermentable feedstock in said fermentation zone toward the drain opening. A collection means (23) disposed beneath the drain opening (165c) continuously collects a portion of the partially converted feedstock and recirculates it through a recirculation system (20) to the uppermost zone (15a).

A withdrawing means (41), communicating with the lower end of the tower (11) continuously withdraws the products of the enzymatic conversion process.

9 Claims, 6 Drawing Figures

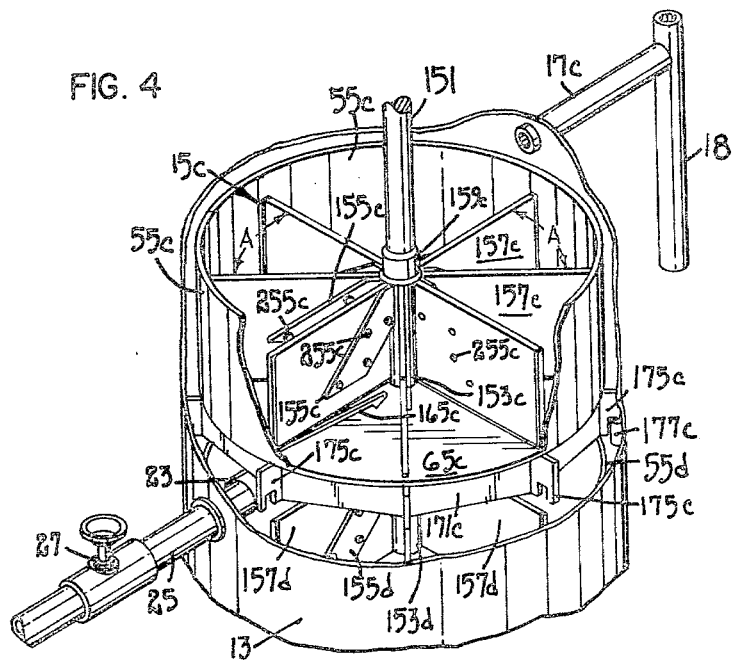
FIG. 4
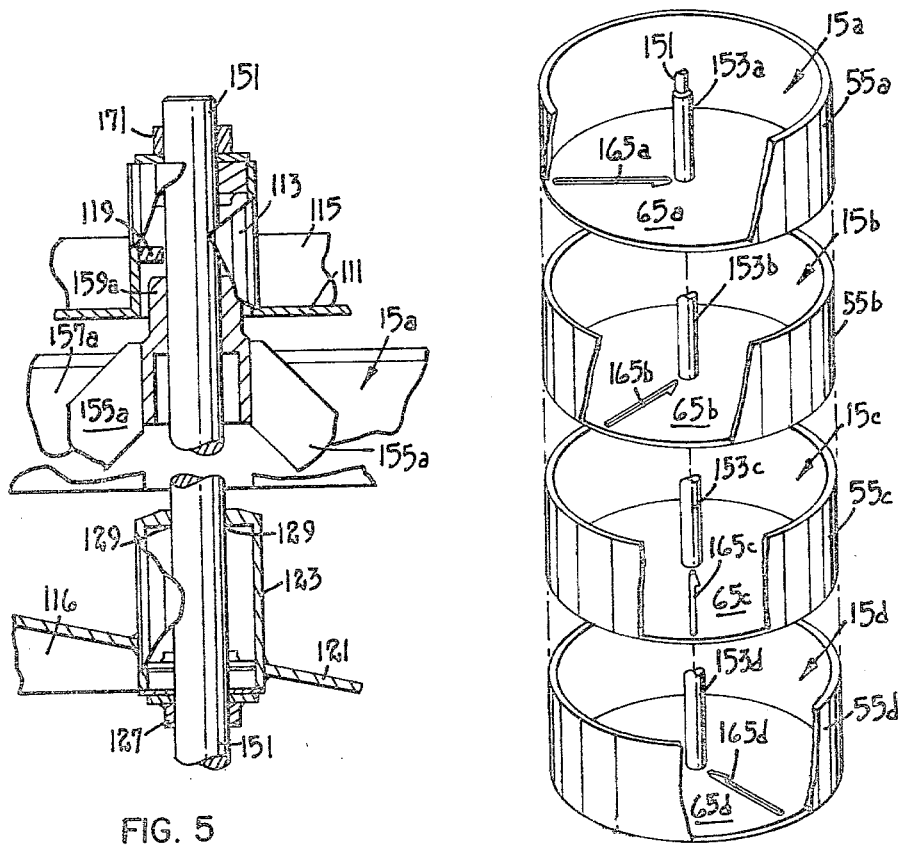
FIG. 5
FIG. 6

CONTINUOUS CHEMICAL CONVERSION OR FERMENTATION APPARATUS

CROSS REFERENCE TO RELATED APPLICATION

Copending application Ser. No. 136,054, filed of even date herewith (Mar. 31, 1980), contains a similar disclosure, and its claims are directed to technologically related subject matter.

TECHNICAL FIELD

This invention relates to an apparatus for the enzymatically-catalyzed conversion of one material to a chemically different material. An aspect of this invention relates to the metabolic conversion of a raw material to useful metabolites and by-products. Another aspect of this invention relates to the fermentation of a fermentable feedstock such as a carbohydrate-containing material and/or the rapid and efficient multiplication of microorganisms in a liquid nutrient medium. An aspect of this invention relates to an apparatus for the fermentation of a fermentable feedstock on a continuous basis (as opposed to a batch basis). Still another aspect of this invention relates to an apparatus for the continuous fermentation of a carbohydrate-containing material with carbohydrase enzymes, which enzymes are preferably supplied by live microorganisms. Still another aspect of this invention relates to an apparatus for the continuous fermentation of a carbohydrate-containing material to produce oxygen-containing aliphatic materials which can be concentrated to provide a combustible fluid suitable for use as a fuel. A still further aspect of this invention relates to an apparatus for continuously converting carbohydrate-containing materials to a "beer" comprising from 1 to about 20% by weight or by volume of an alkanol (preferably ethyl alcohol) dissolved in water.

DESCRIPTION OF THE PRIOR ART

The conversion of carbohydrate-containing materials and other fermentable feedstocks to organic liquids is one of the oldest of the chemical arts. However, the discovery that microorganisms provide the catalytic action for the conversion is a relatively recent discovery going back only to the time of Louis Pasteur. Building upon the monumental discoveries of Pasteur, chemists and microbiologists working in the arts of fermentation (e.g. the manufacture of alcoholic beverages, solvents, fuels, pharmaceuticals, and other techniques involving fermentation or microorganism growth in a liquid nutrient medium) have spent many decades of effort in the optimization of practical processes utilizing these discoveries. For example, a wide variety of microorganism cultures have been investigated, enzymes have been isolated, and new techniques for utilizing and re-utilizing enzymes and cultures have been developed. The design of fermentation apparatus has been carefully studied and improved. For example, it has long been known that even anaerobic fermentation processes produce some carbon dioxide as a fermentation product, and many modern fermentation systems (particularly those outside of the beverage industry) provide means for withdrawing carbon dioxide from the fermentation zone, thereby improving reaction rates or yields and also providing a highly pure form of carbon dioxide as a commercial by-product. Another useful technique in this art involves the use of successive production units, each producing a useful metabolite and a harvested mycelium which can be used as an inoculum in the next production unit in the series. See, for example, U.S. Pat. No. 3,699,840 (Hatcher), issued June 13, 1972.

As in any manufacturing technique or process, fermentation can be carried out on either a batch or a continuous (including semi-continuous) basis. When the objective of the fermentation process is the production of beverages, pharmaceuticals, or even solvents, long retention times in the fermentor may or may not be a serious economic disadvantage. Given the economics of some of these products, a batch process may be suitable.

In the field of fuel production by fermentation (e.g. the manufacture of fuel alcohol from carbohydrates), the skilled technician may be faced with entirely different economic considerations. Even in these days of dwindling petroleum reserves, liquid fossil fuels are still relatively inexpensive compared to, for example, absolute alcohol or even 100–190 U.S. proof alcohol. In this branch of the field of fermentation, batch processes (particularly large-scale batch processes) may be virtually non-competitive with liquid fossil fuels and organic liquid fuels produced by destructive distillation. Accordingly, a continuous fermentation process may yield significant economic benefits in this context.

The design of a continuous fermentation apparatus is by no means straightforward, however. The most readily available types of microorganisms and enzymes (e.g. brewers yeast) typically require long retention times to convert an economically useful amount of carbohydrate (e.g. sugars or starches) to alkanols, ketones, aldehydes, carboxylic acids, and the like. A continuous fermentation apparatus designed to provide a retention time of, say, 24 to 48 hours could be impractically large and cumbersome and not necessarily superior in operation as compared to its batch-type cousin. In any event, all aspects of the fermentation industry can benefit from shorter retention times and relatively simple, efficient fermentation apparatus which is capable of continuously converting a feedstock continuously supplied to the fermentation zone.

SUMMARY OF THE INVENTION

Briefly, this invention relates to an apparatus wherein the conversion or fermentation zone is divided up in at least two different ways. First, the space within the fermentation zone is divided into a plurality of vertically arranged, tray-like fermentation zones for the temporary retention, continuous receiving, and continuous gravity discharge of the fermentable feedstock. Second, each tray-like fermentation zone is further divided into movable segments. In addition, the fermentation apparatus is provided with means for collecting and withdrawing a substantial portion of the broth, "beer", or the like (i.e. the partially fermented feedstock) from the interior of the fermentation apparatus and recirculating it, alone or in combination with fresh feedstock, to the topmost tray-like fermentation zone. A "beer" or water solution containing a useful percentage of liquid fermentation products can then be withdrawn from the lower end of the fermentation zone. The beer can also contain suspended or dispersed solids.

Stated another way, an apparatus of this invention comprises:

(a) a generally vertically disposed conversion of fermentation tower defining a generally vertically extending space containing the plurality of vertically arranged, tray-like fermentation zones, each fermentation zone having a floor with a drain or discharge opening therein for continuous discharge by gravity of the partially fermented feedstock or production medium to the fermentation zone immediately below it, (b) a collection means under one of the drain openings in a fermentation zone for continuously collecting a portion of the partially fermentated feedstock, (c) a feedstock conveying means, communicating with the upper end of the vertically extending space within the tower, which conveying means continuously conveys fermentable feedstock to the uppermost of the fermentation zones, (d) a partially converted feedstock recirculation means for continuously recirculating partially converted or fermented feedstock or production medium collected by the collection means to this uppermost fermentation zone (either directly or via the feedstock conveying means), whereby the fermentable feedstock conveyed to the uppermost of the fermentation zones continuously includes both fresh fermentable feedstock and partially fermented feedstock, and (e) withdrawing means for continuously removing fermentation products from the lower end of the fermentation tower.

Each tray-like conversion or fermentation zone has a generally upwardly extending wall for retaining the convertible feedstock within it, and within this wall there are provided movable partitions, so that this tray-like zone is divided into continuously movable segments for advancing the convertible (e.g. fermentable) feedstock toward the drain opening at a controlled rate and for agitating the partially converted feedstock or production medium. A particularly preferred arrangement involves a set of paddles or vanes or partitions extending radially outward from the center of each tray-like fermentation zone. A single drive shaft can simultaneously rotate all the sets of vanes or paddles in all of the tray-like zones. The rate of rotation of the drive shaft can be set to provide the desired retention time in the tower. It must be remembered, however, that a substantial portion of the total fermentable or convertible material is continuously passing through the recirculation system, thereby increasing the average retention time and thereby also providing the in-coming feedstock with a "head start" due to the high level of enzyme activity in the recirculating material. Still another purpose of the recirculation is to bring the biological catalytic medium (e.g. microorganism culture still in a rapid growth stage), which has progressed at least partway down the tower, into contact with a fresh energy source of fresh fermentable material and/or to recirculate this medium before the relatively toxic matabolites (e.g. alkanols, aldehydes, ketones, etc.) reach a concentration which inhibits further enzymatic or biological activity.

BRIEF DESCRIPTION OF THE DRAWING

In the Drawing, wherein like numerals denote like parts in the various views,

FIG. 4 is a fragmentary perspective view of the conversion or fermentation tower, with portions broken away to show the internal structure of a tray-like conversion or fermentation zone and its movable partitions or vanes;

FIG. 5 is an enlarged fragmentary view of top and bottom seal and bearing housings of the conversion or fermentation apparatus of FIG. 1, with parts broken away to show the internal structure within these housings;

FIG. 6 is an exploded fragmentary perspective view, on a reduced scale, of the internal arrangement of tray-like conversion or fermentation zones, with parts broken away to illustrate the location of drain openings in the various zones.

DETAILED DESCRIPTION

Figure 1:
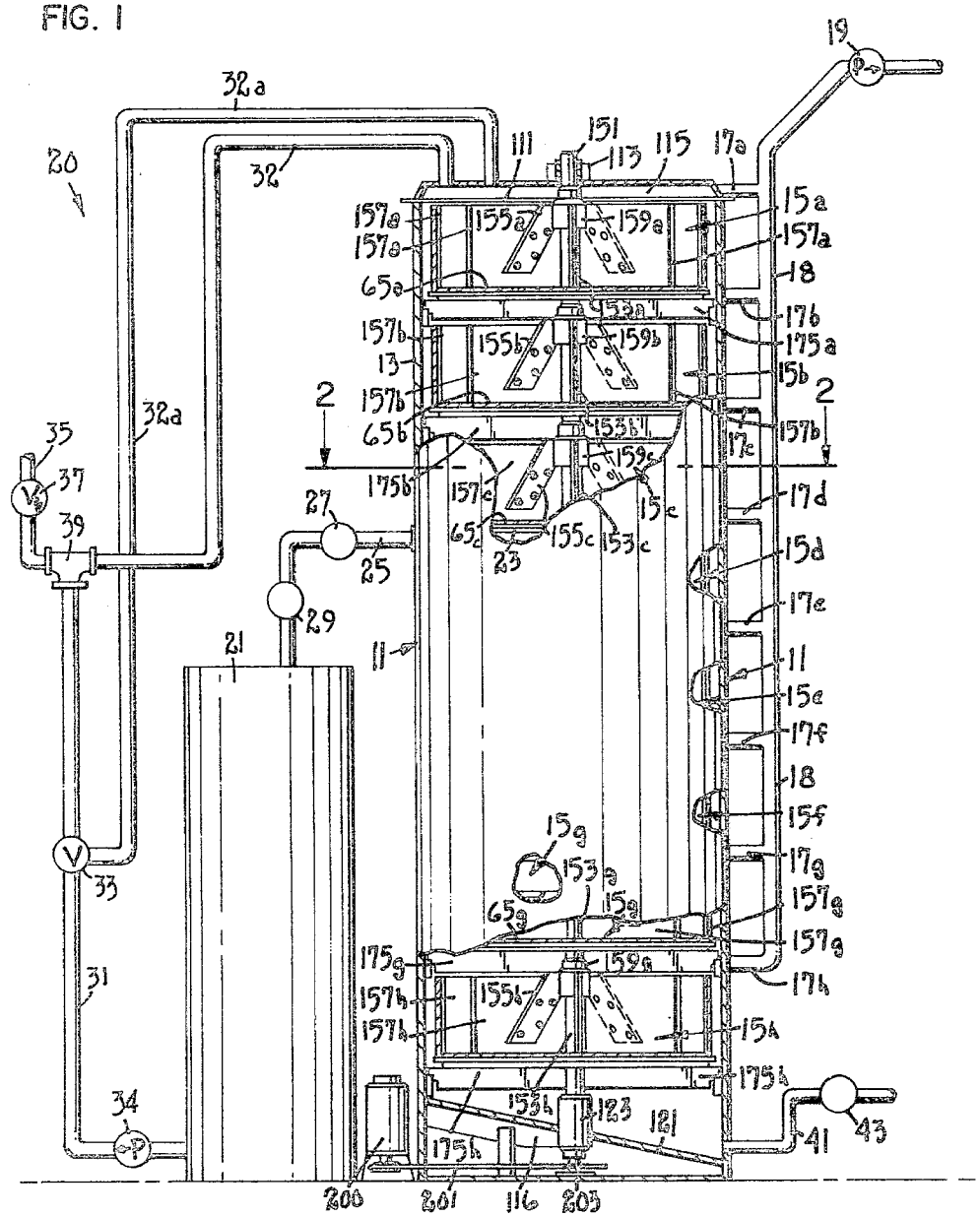
FIG. 1 is a side elevational view of a fermentation or conversion apparatus of this invention with parts broken away to show the internal structure of the fermentation tower.

As will be apparent from the foregoing discussion, this invention contemplates a tower-like, continuously operated convertor or fermentor which can provide, among other things, a generally continuous output of a useful beer from a continuously-supplied convertible (e.g. fermentable) feedstock, even though the total residence time in the tower and the recirculation system is only a few hours or less, e.g. 1 to 20 hours. The fermentation or conversion tower can have a multiplicity of tiers in which conversion (e.g. fermentation) is taking place, and the recirculation system has a capacity sufficient to accomodate at least 10 or 20% of the total capacity of the tower. In a preferred embodiment of this invention, at least 40% of the total production medium in the apparatus is in the recirculation system, substantially the balance being in the tower.

The multiplicity of tiers in the tower comprise the tray-like conversion or fermentation zones. The number of zones, the rate of movement of the fermentation or production medium in the zone, the placement of the drain openings, the number of movable segments in each tray-like zone, and other factors of this sort are determined by the type of production medium (i.e. the substrate upon which the enzyme acts, the type of enzyme and/or microorganism, etc.), the type of fermentation and/or chemical reaction taking place, the type of biological activity desired, the type of desired products, and so forth. Although this invention has utility in the pharmaceutical industry, the solvent manufacturing industry, the alcoholic beverage industry, and other fermentation-oriented industries of this type, the manufacture of a substantially alkanol-based fuel will be selected for discussion in this detailed description, since the features of a suitable fermentation tower and recirculation system for manufacture of alkanol fuel are believed to be illustrative of other fermentation processes. Accordingly, an illustrative feedstock would be carbohydrate-containing, either in the form of material containing carbohydrate per se (e.g. sugars, starches, celluloses and hemi-celluloses, and other mono- and polysaccharides) or glycosides and the like, wherein a polysaccharide chain is linked to a non-carbohydrate nucleus. Generally speaking, an apparatus of this invention is designed primarily to accept a feedstock which has already been broken down or hydrolyzed to monosaccharide, disaccharide, or oligosaccharide units or other polysaccharides (such as starch) which are easily hydrolyzed by chemical or enzymatic means in a very short period of time. In those situations wherein the feedstock requires either lengthy or drastic hydrolytic treatment, there would normally be a preliminary reaction zone, not shown in the Drawing, which would feed into the raw feed conduit 35 (FIG. 1), and the appropriate preliminary reaction apparatus can be of any suitable conventional design. Thus, if the ultimate source of carbohydrate for the feedstock is a starchy mash, a sugar-containing raw material (molasses, whey, etc.) or similar by-product of the food or agricultural industries, an apparatus of this invention would typically be processing a raw feedstock containing mostly the naturally-occurring monosaccharides (glucose, fructose, manose, galactose, gulose, similar aldohexoses and ketohexoses, ribose, similar pentoses), their disaccharides, and their low molecular weight directly fermentable oligomers. Accordingly, the fermentation reactions can be considered to be in progress and in some stage of initiation or completion throughout the entire apparatus and certainly throughout the fermentation tower.

Similarly, the beer or fermentation products withdrawn from the bottom of the tower can be concentrated in any conventional manner, and suitable concentration apparatus can be obtained from commercial suppliers or custom built according to principles well known and well understood in the arts of distillation, solvent extraction, stripping, vacuum evaporation, reverse osmosis, or any other known process for reducing the water content and thereby increasing the organic liquid content of the beer or fermentation product stream. Consequently, the details of the concentration apparatus (distillation column, reverse osmosis module, solvent extraction column, etc.) are outside the scope of this invention. For example, a conventional distillation column will suffice for the manufacture of 100 to 190 U.S. proof fuel alcohol. The conversion of such fuel alcohol to absolute alcohol (e.g. for use in making "gasohol", which is 90% gasoline/10% alcohol, or for solvent use) can be carried out by any conventional technique including ternary azeotropic distillation. Such additional conversions are entirely optional, insofar as the present invention is concerned, particularly in view of the fact that various types of heat engines, space heaters, and the like can be designed to run on almost any organic liquid solution which is combustible and hence a "fuel". Even internal combustion engines can be run on high octane-number or high cetane-number fuels containing, for example, 5 to about 30% by volume of water.

Other devices which are also optional in the context of this invention include conventional equipment for concentrating, liquifying, or solidifying carbon dioxide, a typical by-product of fermentation. (The preferred apparatus of this invention, however, does include means for drawing off carbon dioxide from the interior of the fermentation tower in order to favor the fermentation reactions.) Further optional devices include strippers and rectifiers for the removal of non-potable or toxic or off-flavor chemicals such as aldehydes and ketones. In the manufacture of fuel alcohol, it is unnecessary and may even be undesirable to utilize such strippers and rectifiers, since these chemicals can be useful denaturants and typically have no substantial adverse effect upon volatility, combustibility, heat of combustion, octane rating, and the like. In short, the description of an apparatus of this invention will be focused essentially upon the fermentation tower and the recirculation system. The preferred mode of operation of these major elements of the apparatus will be described subsequently.

Turning now to the Drawing, the continuous fermentation apparatus 10 (i.e. the apparatus for the continuous fermentation of a continuously-supplied stream of fermentable feedstock) is shown most complete in FIG. 1, wherein both the fermentation tower 11 and the recirculation system 20 are illustrated. The recirculation system 20 includes a collection means, in this case a collection trough 23 positioned a little less than half way down the length of the fermentation tower 11. In the embodiment shown in FIG. 1, only one such collection means 23 has been provided. Additional collection means (not shown) can be provided, if desired, which collection means would also communicate with recirculation system 20. Ordinarily, a single collection means 23 is adequate to keep a substantial portion of the total fermentation medium in apparatus 10 continuously flowing through the recirculation system 20. The primary reason for including additional collection means (not shown) would be to give the entire apparatus a greater degree of flexibility. For any given substrate or feedstock, there will be an optimum location for collection means 23. For some substrates and some conditions or desired products, location of the collection means closer to the top of the tower 11 would be more appropriate, for other substrates, conditions, or products, a location closer to or at the bottom would provide better results. Collection means 23 (see also FIG. 4) conveys partially fermented material through conduit 25 and valve 27 and check valve 29 to recirculation reservoir 21, which has a capacity approximately equal to four fermentation zones, e.g. 15a, 15b, 15c, and 15d. The material in reservoir 21 passes through recirculation feed conduit 31 and valve 33 to mixing tee 39, which is an in-line mixing device, bringing about the intimate admixture of raw feed and the partially fermented material from recirculation reservoir 21. The raw feed enters through raw feed conduit 35 and check valve 37 into one leg of mixing tee 39, while the partially fermented material enters through another leg communicating with recirculation feed conduit 31. The third leg of the mixing tee 39 communicates with a feedstock or substrate conveying means, in this case tower feed conduit 32. Alternatively, valve 33 can be used to bypass mixing tee 39 via bypass conduit 32a, which communicates directly with the uppermost fermentation zone 15a. The use of bypass 32a is preferred for sensitive microorganism cultures, e.g. yeasts, a preferred yeast being conventional brewer's yeast or "bottom yeast". The entire recirculation and feed system (including recirculation system 20, the raw feed leg of mixing tee 39 or the bypass 32a, and, if applicable, the tower feed conduit 32) is preferably as water-tight and air-tight as is reasonably practical under the circumstances. If the fermentation apparatus 10 needs to be provided with a source of oxygen for microorganisms or the like which multiply more rapidly under aerobic conditions, it is generally preferred that air or oxygen be introduced upstream of tower feed conduit 32 (optimally upstream of mixing tee 39) so that the aforementioned fluid-tight condition can be maintained throughout apparatus 10. With most of the preferred fermentation processes, aerobic conditions anywhere within fermentation tower 11 entails the risk of excessive carbon dioxide production, with a consequent loss of alkanol, aldehyde, or ketone production.

Fermentation tower 11 includes an outer shell 13 (FIGS. 1 through 4) which defines a generally vertically extending space, which is sufficiently elongated to allow for the stacking or vertical arrangement of a plurality of tray-like fermentation zones 15a, 15b, 15c, etc. Again, the nature of the substrate or feedstock, the nature of the fermentation conditions, the desired products, the desired retention time, and so forth will determine the optimum number of tray-like fermentation zones 15a, 15b, etc. In order to produce a beer containing more than 2% by volume of organic liquid fermentation products in a reasonable time, at least three tray-like fermentation zones (15a through 15c) would ordinarily be preferred. So that the energy requirements for concentrating the beer will not be too unattractive economically, at least six tray-like fermentation zones (15a through 15f) would be continuously operating in a tower constructed according to this invention. The particular tower 11 shown in FIG. 1 has eight such tray-like fermentation zones (15a through 15h), but it will be understood that even more zones can be utilized, depending upon the factors described previously. In the preferred operation of this invention, the retention time in the topmost tray-like fermentation zone 15a is within the range of 5 to 100 minutes, depending upon the speed of rotation of the movable segments within the zone. In the production of fuel alcohol from a mash (corn mash, potato mash, etc.), 10 to 20 minutes would be a more typical retention time. Since, for the sake of simplicity, the rate of rotational movement in each of the additional tray-like fermentation zones (15b through 15h) is the same as that of the topmost zone 15a, a typical flow time from the topmost zone 15a to the inner bottom plate 121 is 80 to 160 minutes, with a substantial portion of the discharge or gravity flow from fermentation zone 15c (30 to 60 minutes down the tower) being withdrawn or tapped off into the recirculation system 20.

Although a pump 34 is used to raise the mixture emerging from mixing tee 39 to the top of tower 11, no pumping is required within the tower 11, and all zone-to-zone movement of fermentation medium is substantially a gravity flow. Indeed, tower feed conduit 32 preferably communicates with the interior space above tray-like fermentation zone 15a, so that gravity flow begins as the feed from conduit 32 enters the upper end of the space defined by shell 13 of tower 11. In this preferred configuration, tower feed conduit 32 passes through top plate 111 of outer shell 13 in a fluid-tight manner. As noted previously, tray-like fermentation zone 15a is divided into movable segments by means of movable partitions or divider vanes or paddles 157a. These partitions 157a rotate about the longitudinal axis of the fermentation tower 11. (Tower 11, its cylindrical outer shell 13, and tray-like fermentation zones 15a through 15h are all cylindrical and concentric with this longitudinal axis.) In the preferred embodiment shown in the Drawing, partitions 157a rotate, while the generally horizontal floor 65a and the vertically extending cylindrical wall 55a of fermentation zone 15a remain stationary. Despite the movement of partitions 157a with respect to the stationary wall 55a and floor 65a, substantially fluid-tight segmentation of zone 15a can be provided by techniques known in the art. Alternatively (but less preferably from the standpoint of convenience of manufacture), partitions 157a, wall 55a, and floor 65a can be a single, integral structure. In this alternative embodiment of a tray-like fermentation zone (not shown), each segment of the tray preferably contains its own drain or discharge opening which is normally closed except for the period of time needed to discharge its contents into the next lower tray at the conclusion of a tray revolution. In the preferred embodiment shown, however, all drain openings are fixed and constantly open. Relocation or rearrangement of drain openings can be provided by removing individual tray-like fermentation zones 15a through 15h and re-inserting them in the tower 11 in different drain opening locations with respect to each other. In the ordinary practice of this invention, however, the location of drain openings would not have to be changed. In the normal practice of this invention, tower feed conduit 32 feeds into that segment of the tray-like fermentation zone 15a which is, at the time it receives the feed, substantially empty and at least three-fourths of a revolution away from the drain opening. The manner in which the segments operate to retain fermentation medium for a controlled period of time will be explained in greater detail in connection with the description of FIGS. 2, 3, 4, and 6.

FIGS. 2-4 and 6 illustrate the operation of the fermentation zone 15c, which receives the discharge or gravity feed or flow from fermentation zone 15b, zone 15b being in turn fed by fermentation zone 15a. This third fermentation zone 15c is selected to illustrate the operation of all tray-like fermentation zones 15a through 15h, since these zones operate in substantially the same manner. In addition, zone 15c illustrates the use of the collection means 23 to tap off a substantial portion of the gravity flow from zone 15c for recirculation through recirculation system 20 to bypass 32a or to mixing tee 39 and tower feed conduit 32. As will be apparent from FIGS. 2 through 4, tray-like fermentation zone 15c is divided into eight segments by movable partitions 157c. Movable partitions 157c all radiate outward from the center of zone 15c. They are rotatable and are rotated by means of paddle arms 155c. Paddle arms 155c are attached to paddles 157c by threaded fastening members 255c. Of course, a variety of means could be used to fasten paddle arms 155c to paddles 157c, but threaded members 255c are convenient, since they permit easier assembly and disassembly of the apparatus. For example, it may be convenient to assemble apparatus 10 "in plant" (i.e. at the production site). Such in-plant assembly can be carried out conveniently by inserting the tray-like fermentation zones 15a through 15h into shell 13 one at a time, with drive shaft 151 in place and with each set of paddles (beginning with paddles 157h) dropped down onto each tray-like fermentation zone (beginning with 15h) and attached to the drive shaft through a linkage including the paddle arms (starting with 155h) and other elements which will now be described.

Figure 3:
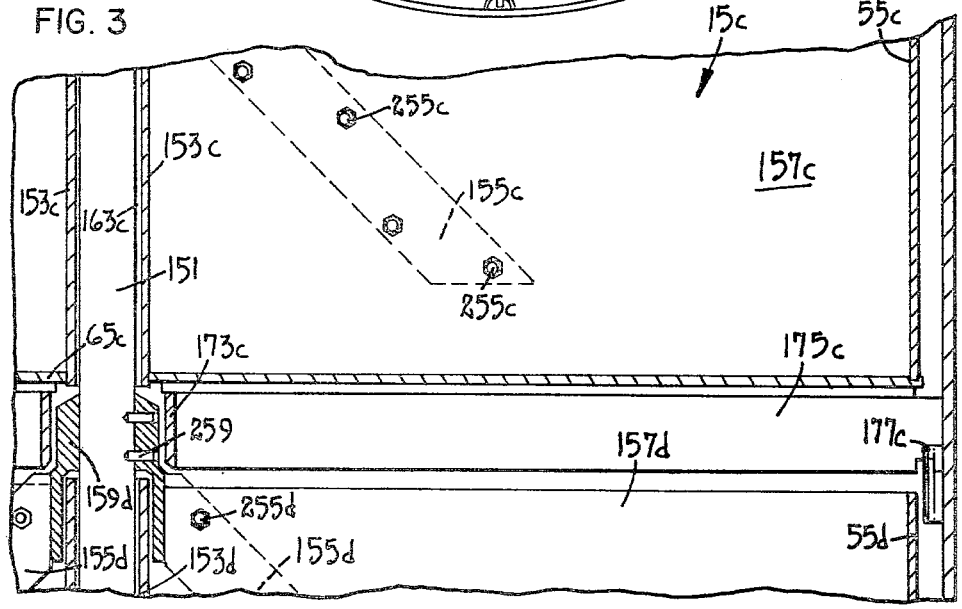
FIG. 3 is an enlarged fragmentary cross-sectional view, taken along line 3—3 of FIG. 2.

In the case of zone 15d, as in the other fermentation zones, paddle arm 155d is integral with a hub 159d which snuggly engages drive shaft 151 and is attached thereto with pins 259 (FIG. 3). Thus, when tray-like fermentation zone 15d and its movable segments are fully assembled, paddles 157d are integral with the paddle arm/hub assembly 155d/159d which is connected to drive shaft 151 at hub 159d. As noted previously, these elements can all be disassembled to permit removal of the movable segments for cleaning, repair, and the like.

The lower end (approximately the lower half) of hub 159d surrounds and encloses a cylindrical vertical sleeve 153d. as shown in FIGS. 3 and 4. Sleeve 153c (FIG. 3) coincides with and defines the central opening 163c in the floor 65c of fermentation zone 15c. This opening 163c and the vertically-extending sleeve 153c which occupies the opening, and openings and sleeves above and below it in overlying and underlying fermentation zones (sleeve 153b of zone 15b, sleeve 153d of zone 15d, etc., best illustrated in FIG. 6) define a generally vertically extending shaft tunnel for drive shaft 151. In addition, sleeve 153c imparts structural integrity to tray-like fermentation zone 15c while defining, in effect, the inner wall of the doughnut-shaped or toroidal zone defined by sleeve 153c in combination with the outer wall 55c. In short, tray-like fermentation zone 15c is preferably a generally vertically-extending toroidal space closed off at its lower end by floor 65c, which floor 65c is a two-dimensional torus. As will be most apparent from FIG. 4, the top edge of paddles 157c is just below the top edge of wall 55c. In operation, the upper or free surface of the fluid fermentation medium in zone 15c preferably is no higher than the topmost edge of paddles 157c and is optimally slightly lower.

Figure 2:
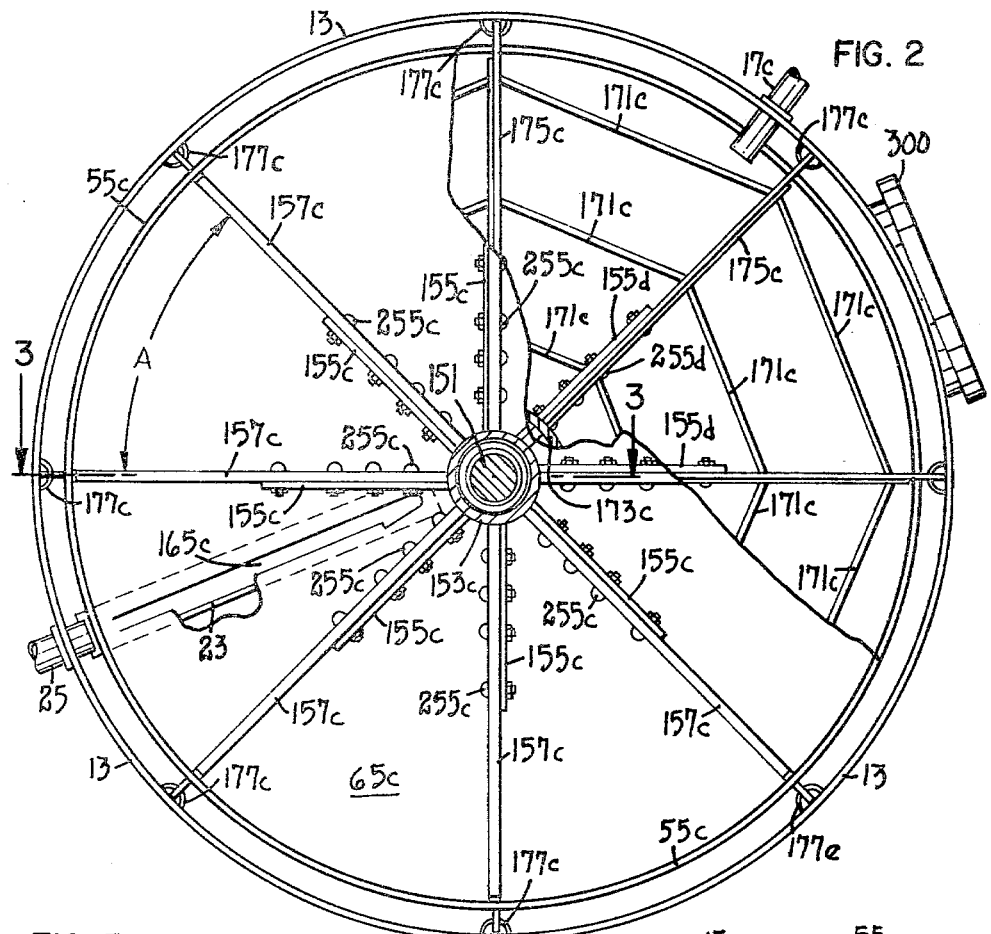
FIG. 2 is an enlarged cross-sectional view taken along line 2—2 of FIG. 1.

As shown in FIGS. 2 and 4, each adjacent pair of paddles 157c, in combination with the subtended portion of wall 55c and sleeve 153c defines a movable segment having an angle or circumferential portion A. In the preferred embodiment shown, angle A is 45°. For efficiency of operation in a reasonable number of fermentation zones, angle A would normally not exceed 180° and typically be not more than 90°. On the other hand, the complexity of the structure of fermentation zone 15c might be greatly increased if angle A were less than 45°. Although many of the elements of fermentation zone 15c can be constructed from relatively lightweight plastics such as polyolefins (even "high density" polyethylene has a specific gravity less than 1.0), at least some of the elements in the zone (e.g. hub 159c) may be constructed of metal (e.g. stainless steel) and, in any event, the total weight of zone 15c filled nearly to the brim with a fermentation medium weighing at least about one kilogram per liter will be extremely heavy and require an adequate support structure. This support structure is illustrated in FIG. 2, wherein a portion of floor 65c has been broken away to show support ribs 175c, extending radially outward from support ring 173c. Braces 171c tie together the radial ribs 175c in a chord-like concentric arrangement which provides additional structural strength. Each radial rib 175c is designed to engage a hanger 177c, much in the manner of a key fitting into a key-way. This rib/hanger engagement fixes the tray-like fermentation zone 15c in the desired position but also permits removal of the tray-like zone 15c, e.g. by hoisting the zone 15c directly upward.

The centrally-located support ring 173c is in register with sleeve 153c and thus also forms a part of the shaft tunnel through which drive shaft 151 runs. As shown in FIG. 3 and FIG. 2, the inside diameter of support ring 173c is slightly larger than the outside diameter of sleeve 153c or even the lower half of hub 159c.

As best shown in FIG. 4, there is sufficient space above the upper edge of wall 55c to allow for communication with suction or degassing conduit or tube 17c, which removes gaseous fermentation products (e.g. carbon dioxide) from fermentation zone 15c and conveys these gaseous products to the suction or degassing manifold 18. There is also sufficient space below floor 65c of zone 15c and above the upper edge of wall 55d to allow for the placement of trough 23, which collects a substantial portion of the downward flow from zone 15c and conveys it, through conduit 25 and valve 27 to the recirculation system 20 (FIG. 1). As best shown in FIG. 2, the elongated drain opening 165c in floor 65c is located immediately above trough 23, so that much of the fermentation medium draining through drain opening 165c will fall into trough 23. Drain opening 165c is substantially, but not exactly, radially oriented with respect to the center of floor 65c. Thus, drain opening 165c is offset from but generally parallel and in closely spaced relation to a radius extending from the center of floor 65c, i.e. from the generally vertical axis of fermentation tower 11. By means of this slight offsetting of drain opening 165c, a clockwise motion of paddle 157c will result in exposure of the end of drain opening 165c which is located closest to the center of floor 65c. When the fermentation medium within fermentation zone 15c has a very low viscosity (e.g. a vicosity in the hundreds of centipoise or less), a large amount of the fermentation medium within the moving segment approaching drain opening 165c will drain out as soon as paddle 157c has crossed over the end of opening 165c adjacent the center of floor 65c. For a high viscosity fermentation medium, a drain opening which is exactly radially oriented might be preferable. However, it has been found that the viscosity of, for example, a corn mash mixed with water is not very different from water itself. (Apparently, the tiny particles of corn mash do not have a thixotropic effect with respect to the aqueous phase of the fermentation medium).

It may be desirable to observe the operation of the interior of fermentation tower 11, and a sealed porthole 300 (FIG. 2) provided with a glass or plastic lens (not visible in FIG. 2) is included in the structure of shell 13 for this purpose. An additional advantage of porthole 300 is that further conduits, troughs, or the like can be inserted into the interior of fermentation tower 11 using suitable peripheral sealing collars or the like (not shown), thereby avoiding the necessity or cutting through shell 13 if such additional elements become desirable after the construction of tower 11 is complete.

As noted previously, it is ordinarily desirable to exclude the ambient atmosphere from the interior of tower 11, even when the fermentation processes taking place within tower 11 are not exclusively anaerobic. Furthermore, it is desirable that the interior of tower 11 be under subatmospheric pressure to assist in the degassing via suction tubes or conduits 17a–17h and manifold 18. Yet, in the embodiment shown, drive shaft 151 extends along the entire vertical axis of tower 11 and is driven by a motor 200 and chain drive means 201 located outside of the sealed subatmospheric interior space defined by shell 13 of tower 11. For convenience of illustration, the motor 200 and the chain drive 201 are shown at the bottom of tower 11. In actual practice, it may be convenient to drive the drive shaft 151 from at its top end. To provide bearings for drive shaft 151 and to prevent leakage of ambient air into the aforementioned sealed inner space, seal and bearing housings 113 and 123 (FIGS. 1 and 5) are included within the structure of tower 11.

Turning to FIG. 5, top seal and bearing housing 113 is a substantially cylindrical projection extending upwardly from top plate 111. Reinforcing rib 115 also extends upwardly from top plate 111 and radially outward from housing 113. Housing 113 is provided with a seal 119 which prevents leakage of ambient air into the interior of tower 11 by sealingly engaging the outer surface of drive shaft 151. This sealing engagement does not prevent rotation of drive shaft 151, however. The upper end of drive shaft 151 is held in the desired orientation by bearing 117, which also permits rotation of drive shaft 151.

FIG. 5 also illustrates the structure of bottom seal and bearing housing 123, which is similar in design and in concept to the top housing 113. The bottom seal and bearing housing 123 extends both upwardly and downwardly from inner bottom plate 121. Above plate 121, the vacuum and ambient air exclusion conditions are maintained. Providing these conditions above bottom plate 121 is desirable, since, while only a very minor amount of fermentation (if any) may be taking place in the space immediately above plate 121, this plate 121 nevertheless serves as a catch trough for the discharge from lowermost fermentation zone 15h (FIG. 1). Bottom plate 121 is slanted downwardly so as to direct the flow of the beer into a suitable withdrawing means, in this case beer conduit 41. (The beer is pumped by pump 43 to a conventional apparatus for further processing of the beer, including concentration of the organic liquids in the beer; see FIG. 1.)

Returning to FIG. 5, housing 123 is provided with bottom seal 129 and bottom bearing 127, which are similar in design to top seal 119 and top bearing 117. As noted previously, the drive means for drive shaft 151 (i.e. motor 200 and drive chain 201) can therefore be located outside of the sealed interior of tower 11. Drive chain 201 can engage the lower end of drive shaft 151 by any suitable means such as the sprocket 203 shown in FIG. 1. To provide additional support for the tower structure, a brace or rib 116 radiates from the outer surface of housing 123 out to the inside surface of shell 13.

It will be understood that the foregoing description of the tower, the recirculation/feed system, the degassing system, and the beer withdrawal system is merely illustrative, and modifications can be made to better accomodate and process various feedstocks, fermentation products, and the like. For example, if the enzymes catalyzing the conversion of the feedstock produce primarily gaseous fermentation products such as methane rather than liquid fermentation products such as ethyl alcohol, fused oil, or aldehydes and ketones, withdrawing means 41 can be designed to remove residues, while manifold 18 can be designed to collect the gaseous products.

Operation of the Apparatus

The incoming mash or other fermentable feedstock is preferably blended with an active microorganism culture before passing through check valve 37. Partially fermented material and the highly active, rapidly growing culture are preferably conveyed to the first tray-like fermentation zone 15a via bypass 32a, while the flow from valve 37 is conveyed to zone 15a though conveying means or conduit 32. The gravity feed from conduits 32 and 32a falls into a movable segment of zone 15a defined by a pair of adjacent paddles 157a. This segment rotates through almost a full revolution before reaching the drain opening and discharging into zone 15b. A similar sequence of events occurs in zone 15b and the fermentation medium then drops through the drain in zone 15b into the movable segment just "beyond" drain opening 165c in zone 15c. This movable segment describes about $\frac{7}{8}$ of a revolution (about 315°) before its leading paddle 157c reaches drain opening 165c, from which the fermentation medium drains, partly into zone 15d and partly into trough 23. The material in trough 23 exits through shell 13 via conduit 25 and into the recirculation system 20, from which it flows via bypass 32a to tower 11, to begin a new pass through zones 15a, 15b, etc., starting with zone 15a. The material collected in trough 23 contains a vastly multiplied microorganism culture. In short, at least the first three fermentation zones 15a, 15b, and 15c provide fermentation, agitation, and organism multiplication in this preferred mode of operation, thereby providing a high ratio of active microorganisms to fermentable material.

The fermentation medium in zone 15d continues to rotate and flow downward through zones 15e, 15f, 15g, and 15h of tower 11 until it is discharged from the lowermost zone 15h onto inner bottom plate 121, which acts as a catch trough feeding the beer conduit 41. The location of drain openings 165a, 165b, etc. is illustrated in FIG. 6.

Assuming for the sake of illustration that the drain opening in zone 15a is generally at 270° of the circle of rotation of drive shaft 151, and assuming a clockwise rotation of drive shaft 151 from 270° through 315°, 360°, 45°, 90°, 135°, etc., the fixed drain openings (165b, 165c, 165d, etc.) will be located as follows with respect to 270° in zone 15a: 165b (FIG. 6) at 225°, 165c at 180° (FIG. 6), 165d (FIG. 6) at 135°, 165e (not shown) at 90°, 165f (not shown) at 45°, 165g (not shown) at 0°, and 165h (not shown) at 315°. As will be apparent from FIG. 6, the clockwise-rotating segment in zone 15b which has just passed 225° will receive a gravity feed from zone 15a. This segment will then be out of register with the drain opening and will pass through 360° and all the way around to 225° before coming into register and discharging into zone 15c. (In other words, the material discharged into zone 15b is retained for about $\frac{7}{8}$ of a full revolution of drive shaft 151.) The segment of zone 15c receiving the discharge from zone 15b will have just passed 180°, i.e. just "beyond" opening 165c, and will have to pass through 360° and around to 180° before reaching the portion of floor 65c which has opening 165c. The material retained in this segment will then drain out into trough 23 and zone 15d. The segment of zone 15d receiving the discharge will have just passed 135° and will have to rotate about $\frac{7}{8}$ of a revolution to reach the drain opening. The sequence of events in zone 15d is repeated for zones 15e, 15f, 15g, and 15h, as indicated previously.

The beer withdrawn from the inner bottom plate 121 will typically be a water solution containing, for example, about 3–20% by weight of ethyl alcohol and relatively smaller amounts of acetaldehyde, acetone, acetic acid, and fusel oil. Yet the time required to traverse the entire height of tower 11 could be as short as about an hour or two. Furthermore, the vacuum within shell 13 can be continuously maintained, the feedstock continuously introduced through conduit 32, and the beer continuously withdrawn through conduit 41.

The attainment of a useful beer is not the only possible manufacturing objective where apparatus 10 is concerned. Apparatus 10 can also be considered to be a means for producing, as its primary product, live or killed organism cultures (e.g. bacteria, molds, yeasts, etc.), enzymes, fertilizers, feeds, human-edible material, etc., with carbon dioxide or combustible organic liquids or gases being merely a desirable by-product. Stated another way, apparatus 10 can serve as a device for (a) increasing the protein content (or de-sugaring or de-starching) of starchy materials such as corn mash and potato mash, and/or (b) increasing the multiplication rate of live microorganism colonies (yeasts, molds, bacteria, etc.). If desired, these live colonies can be, at least to some extent, recirculated more or less indefinitely through tower 11, thereby increasing their hardiness and efficiency.

For large-scale production of a tower 11 of this invention, it is desirable to simplify the design of the interior of the tower. For example, the upwardly-extending cylindrical walls 55a, 55b, 55c, etc. of zones 15a, 15b, 15c, etc. can be nonintegral with the zone floors 65a, 65b, etc., but integral with outer shell 13—or even eliminated entirely, whereby the upwardly-extending cylindrical walls 55a, 55b, etc. for each zone 15a, 15b, etc. can be the interior surface of shell 13 itself. In this embodiment (not shown), each floor 65a, 65b, 65c, etc. is provided with a peripheral sealing member (e.g. a rubbery element) which sealingly engages the interior surface of shell 13. With the proper fluid-tight sealing engagement of interior of shell 13 and the periphery of each floor 65a, 65b, etc., the support structure for each floor can be provided in a manner substantially similar to that shwon in FIG. 2 Drawing, i.e. radial ribs 175, hangers 177, braces 171, and support ring 173. This large-scale production embodiment is also advantageous when manufacturing the entire interior of tower 11 out of stainless steel (for use in making food-grade products). Although tower 11 is normally designed to maintain anaerobic conditions in zones 15a through 15h, gases (e.g. air, $O_2$, $CO_2$) can be deliberately introduced into one or more zones to hinder or accelerate reactions or biological action taking place in the zones.

What is claimed is:

1. An apparatus for the continuous conversion of a continuously-supplied convertible feedstock comprising:
   (a) a generally vertically disposed conversion tower defining a generally vertically extending space containing a plurality of vertically arranged, tray-like conversion zones for the temporary retention, continuous receiving, and continuous gravity discharge of a convertible feedstock, each said conversion zone being defined by a generally horizontal floor having (1) a drain opening therein for the continuous discharge by gravity of partially converted convertible feedstock to the conversion zone disposed therebelow and (2) a generally upwardly extending wall for retaining said convertible feedstock therewithin, each said conversion zone being divided into substantially liquid-tight, continuously movable segments by movable partitions for advancing the convertible feedstock in said conversion zone toward said drain opening at a controlled rate,
   (b) a collection means, disposed beneath a said drain opening in a said conversion zone, for continuously collecting a portion of the partially converted convertible feedstock discharged through said drain opening,
   (c) a feedstock conveying means, communicating with the vertically extending space defined by said tower, for continuously conveying convertible feedstock to a said conversion zone,
   (d) a partially converted feedstock recirculation means for continuously circulating partially converted convertible feedstock collected by said collection means to a said conversion zone, whereby the convertible feedstock conveyed to the said conversion zone continuously includes both fresh convertible feedstock and partially converted convertible feedstock, and
   (e) withdrawing means, communicating with the lower end of said vertically extending space, for continuously withdrawing products from said lower end of said vertically extending space.

2. An apparatus according to claim 1 comprising:
   (a) a generally hollow, generally cylindrical tower containing at least three tray-like fermentation zones arranged generally concentrically along a generally vertical axis, each said tray-like fermentation zone comprising:
      (1) a generally horizontal floor having a generally radial elongated drain opening and a generally centrally located opening therein, the generally vertical series of generally centrally located openings in said tray-like fermentation zones defining a generally vertical shaft tunnel extending along said generally vertical axis,
      (2) a generally cylindrical wall extending upward from the periphery of said floor,
      (3) a plurality of generally radially disposed, upwardly extending movable partitions for generally radially dividing said tray-like fermentation zone into movable segments, said movable partitions being in generally water-tight relationship to said floor and said generally cylindrical wall, said movable partitions being generally radially disposed with respect to the center of said tray-like fermentation zone, and
   (b) a drive shaft means, disposed along said generally vertical axis and connected to each plurality of said partitions in each said tray-like fermentation zone, for rotating said partitions about said generally vertical axis.

3. An apparatus according to claim 2 wherein the elongated drain openings in the floor of said tray-like fermentation zones are out of register with each other, whereby a segment of a said fermentation zone receiving a discharge of fermentable feedstock from the fermentation zone immediately thereabove must rotate at least about three-fourths of a complete revolution before reaching the elongated drain opening in said fermentation zone receiving the discharge, thereby retaining the thus-received fermentable feedstock in a given fermentation zone for at least the time required for a said partition to make three-fourths of a full revolution.

4. An apparatus according to claim 3 wherein each said elongated drain opening is offset from but generally parallel and in closely spaced relation to a radius extending from said generally vertical axis.

5. An apparatus according to claim 1, wherein said apparatus comprises at least six said tray-like fermentation zones, and each said zone is divided into at least four of said continuously movable segments.

6. An apparatus according to claim 1 wherein each said generally horizontal floor remains stationary while said movable partitions are moving, and said drain opening continuously remains in a fixed position relative to the movement of said movable partitions.

7. An apparatus according to claim 1 wherein said generally vertically extending space in said fermentation tower is essentially sealed off from the ambient atmosphere to provide generally anaerobic conditions within said fermentation tower.

8. An apparatus according to claim 1 wherein the top edges of said movable partitions are in closely spaced relation to the top edge of said generally upwardly extending wall.

9. A continuous fermentation apparatus for the continuous fermentation of a carbohydrate-containing feedstock with a live microorganism culture capable of secreting carbohydrase enzyme, comprising:
   (a) a raw feed conduit for providing a combined flow comprising an essentially unfermented carbohydrate-containing feedstock and said live microorganism culture and for conveying said combined flow to the interior of said continuous fermentation apparatus,
   (b) an elongated vertically extending cylindrical fermentation tower having an outer cylindrical shell defining an elongated vertically extending space having at least six tray-like fermentation zones arranged vertically and concentrically along the vertical longitudinal axis of said outer cylindrical shell, each said tray-like fermentation zone comprising:
      (1) a generally horizontal floor having a generally radial elongated drain opening and a generally centrally located opening therein, the generally vertical series of generally centrally located openings in said tray-like fermentation zones defining a generally vertical shaft tunnel extending along said generally vertical axis,
      (2) a generally cylindrical wall extending upward from the periphery of said floor,
      (3) a plurality of generally radially disposed, upwardly extending movable partitions for generally radially dividing said tray-like fermentation zone into substantially liquid-tight, movable segments, said movable partitions being in generally water-tight relationship to said floor and generally cylindrical wall,
   (c) a drive shaft means, disposed along said generally vertical axis and connected to each plurality of said partitions in each said tray-like fermentation zone, for rotating said partitions about said generally vertical axis,
   (d) means for rotating said drive shaft means at the rate of about 0.01 to about 0.2 revolutions per minute,
   (e) a collection means, disposed beneath a said drain opening in a said generally horizontal floor, for continuously collecting the mixture of partially fermented carbohydrate feedstock and live microorganisms passing through said drain opening,
   (f) partially fermented carbohydrate feedstock recirculation means, communicating with said collection means, for continuously recirculating the thus-collected mixture to essentially the upper end of said elongated vertically extending space,
   (g) beer conduit means, communicating with the space below the generally horizontal floor of the lowermost of said tray-like fermentation zones, for withdrawing an alkanol-containing beer from said fermentation tower, and
   (h) degassing conduit means, communicating with the interior of elongated vertically extending space, for withdrawing gaseous fermentation products from said fermentation tower.

* * * * *